United States Patent [19]
Jannard et al.

[11] Patent Number: 5,760,868
[45] Date of Patent: Jun. 2, 1998

[54] UNITARY HINGELESS EYEGLASS FRAME

[75] Inventors: James H. Jannard, Eastsound, Wash.; Peter K. Yee, Irvine, Calif.

[73] Assignee: Oakley, Inc., Foothill Ranch, Calif.

[21] Appl. No.: 672,104

[22] Filed: Jun. 27, 1996

[51] Int. Cl.$^6$ .................................................. G02C 5/22
[52] U.S. Cl. ........................... 351/153; 351/41; 16/228
[58] Field of Search .................... 351/41, 44, 153; 16/228

[56] References Cited

U.S. PATENT DOCUMENTS

| | | | |
|---|---|---|---|
| D. 200,735 | 3/1965 | Mitchell | 351/44 |
| D. 324,394 | 3/1992 | Jannard | D16/102 |
| D. 325,040 | 3/1992 | Jannard | D16/102 |
| D. 328,468 | 8/1992 | Jannard | D16/101 |
| D. 329,445 | 9/1992 | Jannard | D16/116 |
| D. 330,716 | 11/1992 | Jannard | D16/116 |
| D. 331,587 | 12/1992 | Jannard et al. | D16/123 |
| D. 331,763 | 12/1992 | Jannard | D16/101 |
| D. 333,145 | 2/1993 | Jannard | D16/101 |
| D. 369,375 | 4/1996 | Jannard et al. | D16/326 |
| 2,027,037 | 1/1936 | Gottlieb | 351/41 |
| 2,280,666 | 4/1942 | Schofield | 351/41 |
| 2,986,970 | 6/1961 | Kilgour | 351/41 |
| 3,361,514 | 1/1968 | Davis | 351/63 |
| 3,475,083 | 10/1969 | Gitlin et al. | 351/41 |
| 3,526,449 | 9/1970 | Bollé et al. | 351/44 |
| 3,649,106 | 3/1972 | Hirschmann, Jr. | 351/117 |
| 3,701,591 | 10/1972 | Wichers | 351/41 |
| 4,602,856 | 7/1986 | Marks | 351/44 |
| 4,681,410 | 7/1987 | Paulsen | 351/63 |
| 4,730,916 | 3/1988 | Liautaud et al. | 351/117 |
| 4,740,069 | 4/1988 | Baum | 351/57 |
| 5,137,342 | 8/1992 | Jannard et al. | 351/123 |
| 5,208,614 | 5/1993 | Jannard | 351/41 |
| 5,249,001 | 9/1993 | Jannard | 351/123 |
| 5,610,668 | 3/1997 | Mage | 351/62 |

FOREIGN PATENT DOCUMENTS

| | | |
|---|---|---|
| 198971 | 8/1958 | Anguilla . |
| 1402367 | 5/1965 | France . |
| 423641 | 2/1935 | United Kingdom . |

*Primary Examiner*—Huy Mai
*Attorney, Agent, or Firm*—Knobbe, Martens, Olson & Bear, LLP

[57] ABSTRACT

Disclosed is a hingeless eyeglass frame designed so the entire eyeglass frame provides a medially directed force at the posterior portion of the earstems to increase the retentive force between the eyewear and the head. In one vented embodiment, each lens of a dual-lens eyeglass is provided with a plurality of apertures extending therethrough, at the junction between the lens and the surrounding frame. The unitary frame or conventionally hinged frames may also have apertures to allow airflow for ventilation.

16 Claims, 3 Drawing Sheets

UNITARY HINGELESS EYEGLASS FRAME

The present invention relates generally to eyewear, and more particularly to a hingeless eyeglass frame adapted to provide a medially and anteriorly directed force at the posterior portion of the earstems to retain the eyewear on the wearer's head.

BACKGROUND OF THE INVENTION

A wide variety of improvements have been made in recent years in the eyewear field, particularly with respect to eyewear intended for use in active sports or as fashion sunglasses. For example, certain improvements have been incorporated into eyewear having a unitary lens, such as the "Blades®" design (Oakley, Inc.) the "M Frame®" line (Oakley, Inc.), and the "Zero®" line also produced by Oakley, Inc. These eyewear designs accomplish a variety of functional advantages, such as maximizing interception of peripheral light, reducing optical distortion and increasing the wearer's comfort level, compared to previous active sport eyewear.

Lens geometry has also been the subject of a variety of innovations. The unitary lens of the "Blades®" eyewear incorporates the cylindrical geometry disclosed, for example, in U.S. Pat. No. 4,859,048, issued to Jannard. This geometry allows the lens to closely conform to the wearer's face and intercept light, wind, dust, etc. from directly in front of the wearer (anterior direction) and peripherally (lateral direction). See also U.S. Pat. No. 4,867,550 to Jannard (toroidal lens geometry).

A variety of improvements in eyewear retention systems have also been made in recent years. See, for example, U.S. Pat. No. 5,137,342 to Jannard et al. and No. 5,249,001 to Jannard. Nonetheless, the need remains for further improvements in comfortable eyewear retention systems which are useful in highly active sports.

Another remaining practical problem confronting the wearer is how to store eyeglasses when the eyeglasses are not being worn. For example, a wearer may be continually putting sunglasses on and off as the wearer goes indoors and outdoors. Although eyeglasses are often supplied with a storage case, the case is one more item the wearer must carry. Prior art efforts include attaching a string to each end of a temple and hanging the string around the wearer's neck. This can be inconvenient or distracting as the eyeglasses tend to swing around at the end of the string as the wearer moves about.

In addition, ventilation has become an issue with a number of recent eyewear designs. Early dual-lens eyeglass systems generally comprised a right and left lens suspended by an eyeglass frame in the wearer's line of sight. Each of the right and left lenses was generally disposed on a plane which was perpendicular to the wearer's normal or "straight ahead" line of sight. Although the upper portion of the eyeglass frame often contacts the forehead, a significant ventilation gap was normally present between the lower and lateral edges of the eyeglass lens and the wearer's cheek bone.

Dual lens eyeglasses have more recently been developed in which the eyeglasses exhibit a significant rake and wrap compared to the prior art. Lens rake refers to the extent to which the lower edge of a lens curves in towards the wearer's face. Lens wrap refers to the extent to which the lateral edge of the lens curves rearwardly to conform more closely to the side of the wearer's head.

Increased lens rake and wrap have as a consequence a reduction in the gap between the lower edge of the lens and the face as well as a reduction in the gap between the lateral edge of the lens and the face.

Although increased rake and wrap in dual-lens eyeglasses can produce a variety of benefits, one disadvantage is the entrapment of a relatively small volume of air between the lens and the wearer's face. When someone wears eyeglasses of high wrap and rake design during active sports, such as skiing, bicycling or the like, the lenses are susceptible to fogging on the inside surface due to an inadequate ability to circulate moisture-laden air.

Thus, there remains a need for improved eyewear with improved retention and convenient short term storage when the eyewear is momentarily removed. Preferably, the eyewear design permits either a unitary lens or a dual lens eyeglass system having a relatively high level of rake and wrap compared to the prior art, which minimizes the risk of fogging due to the entrapment of air between the lens and the face of the wearer.

SUMMARY OF THE INVENTION

There is provided in accordance with one aspect of the present invention a unitary eyeglass frame for securing an eyeglass lens to the head of the wearer, and for positioning the lens in the wearer's line of sight, the unitary frame in combination with the lens adapted to maintain a medially directed bias on the distal (posterior) end of the earstem over a wide range of lateral positions, thereby accommodating a wide range of head widths. When the glasses are not being worn to position the lens in the wearer's line of sight, the unitary eyeglass frame can be hung around the wearer's neck or on top of the wearer's head for storage.

One embodiment of the eyeglass frame comprises an arcuate lens support section for extending across the front of the wearer's face to support at least one lens in the wearer's line of sight. The support section has a central zone and first and second lateral zones.

First and second earstems extend from the first and second lateral zones such that when the frame is on the wearer's head and the lens is in the wearer's line of sight the first and second earstems extend rearwardly from the lens support section past the wearer's ears and toward each other part way around the back of the wearer's head. The eyeglass frame is a hingeless, unitary construction.

Preferably, the first and second earstems are provided with first and second ends spaced apart from the lens support section, and the first and second ends are separated from each other by no more than about 4 inches, preferably no more than about 3½ inches and more preferably no more than about 3 inches in the relaxed, unworn configuration. In an alternate embodiment, the first and second ends are separated by no more than about 2½ inches, and preferably no more than about 2 inches in the relaxed, unworn configuration.

The first and seconds ends are moveable in a lateral direction with respect to each other throughout a lateral range of motion to a sufficient separation distance to accommodate the head of a wearer, such as at least about 4 inches and preferably as much as 5 inches or more while maintaining a medially directed bias throughout the lateral range of motion.

In accordance with a further aspect of the present invention, there is provided a vented eyeglass frame. The vented eyeglass frame comprises a front, lens support section and first and second rearwardly extending earstems. At least a first and a second forward facing apertures are provided in the frame, the first aperture disposed between the first earstem and the lens support section, and the second aperture is disposed between the second earstem and the lens support section. The vented frame may be provided with either a single unitary lens, or dual lenses. The vented frame may also be provided on a hingeless frame design, or on a design which comprises hinged connections between the earstem and other portions of the eyeglass frame.

In accordance with a further aspect of the present invention, there is provided a vented dual lens eyeglass system. The eyeglass system comprises a hingeless eyeglass frame having a lens support section and a pair of earstems. At least one aperture is provided through a proximal end of each said earstems to provide first and second frame vents. A right and a left lens each having a central optical zone and a peripheral edge are additionally provided in the hingeless eyeglass frame. Preferably, at least one recess extends into each lens from the peripheral edge thereof towards the optical zone to provide a vent through the lens. The hingeless frame contacts the peripheral edge of the lens on a first side and on a second side of the recess, and extends across the recess to enclose the lens vent. Preferably, multiple vents are provided spaced around the periphery of the lens.

Further features and advantages of the present invention will become apparent from the detailed description of preferred embodiments which follows, when considered together with the attached claims and drawings.

DETAILED DESCRIPTION OF THE PREFERRED EMBODIMENTS

As used in the present application, "eyewear" is a general term intended to embrace optical devices containing corrective lenses for defects in vision or noncorrective lenses for such special purposes as filters for absorbing or blocking portions of the electromagnetic spectrum, and/or providing physical shields for the eyes.

The term "unitary" frame refers to either a frame which is one piece in the as molded condition or a frame which is fabricated from two or more parts such that as a practical matter in the intended use environment it functions like a hingeless structure. An important aspect of the unitary frame feature of the invention is the absence of a conventional hinge. This hingeless construction can be achieved through the use of one-piece or multiple-piece construction techniques as will be apparent to those of skill in the art in view of the disclosure herein.

Figure 1:
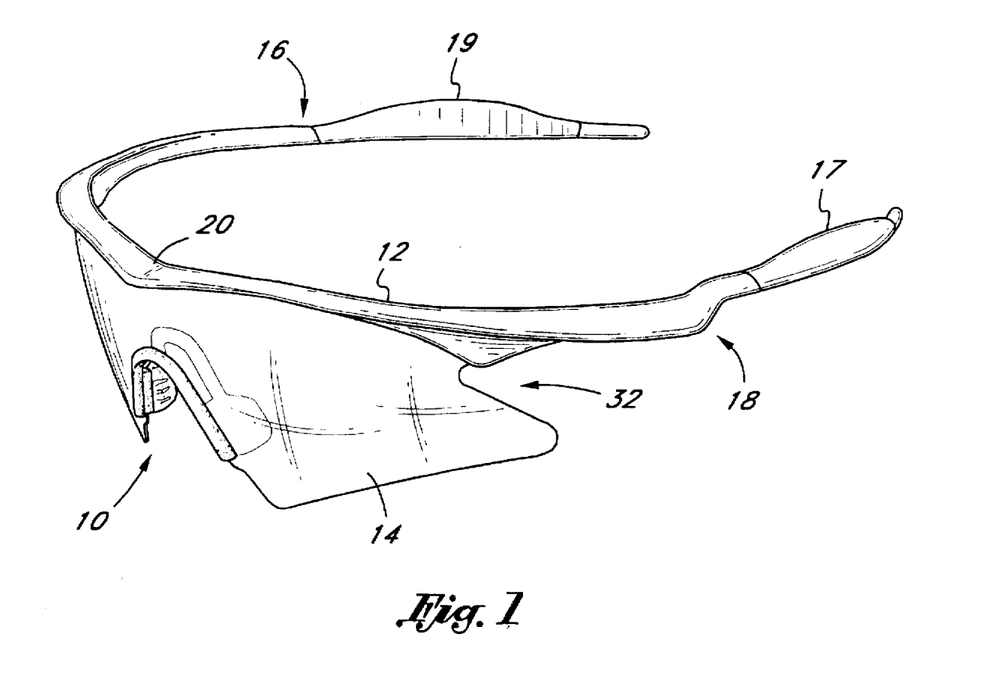
FIG. 1 is a perspective view of unitary lens eyewear embodying the hingeless frame of the present invention.

As shown in FIG. 1, eyewear 10 adapted to position a lens 14 in a predetermined orientation relative to the eyes, includes a frame 12, lens 14 and earstems 16 and 18. Preferably, the lens 14 is joined to the frame 12 so as to position the lens 14 before at least the primary line of sight.

Figure 2:
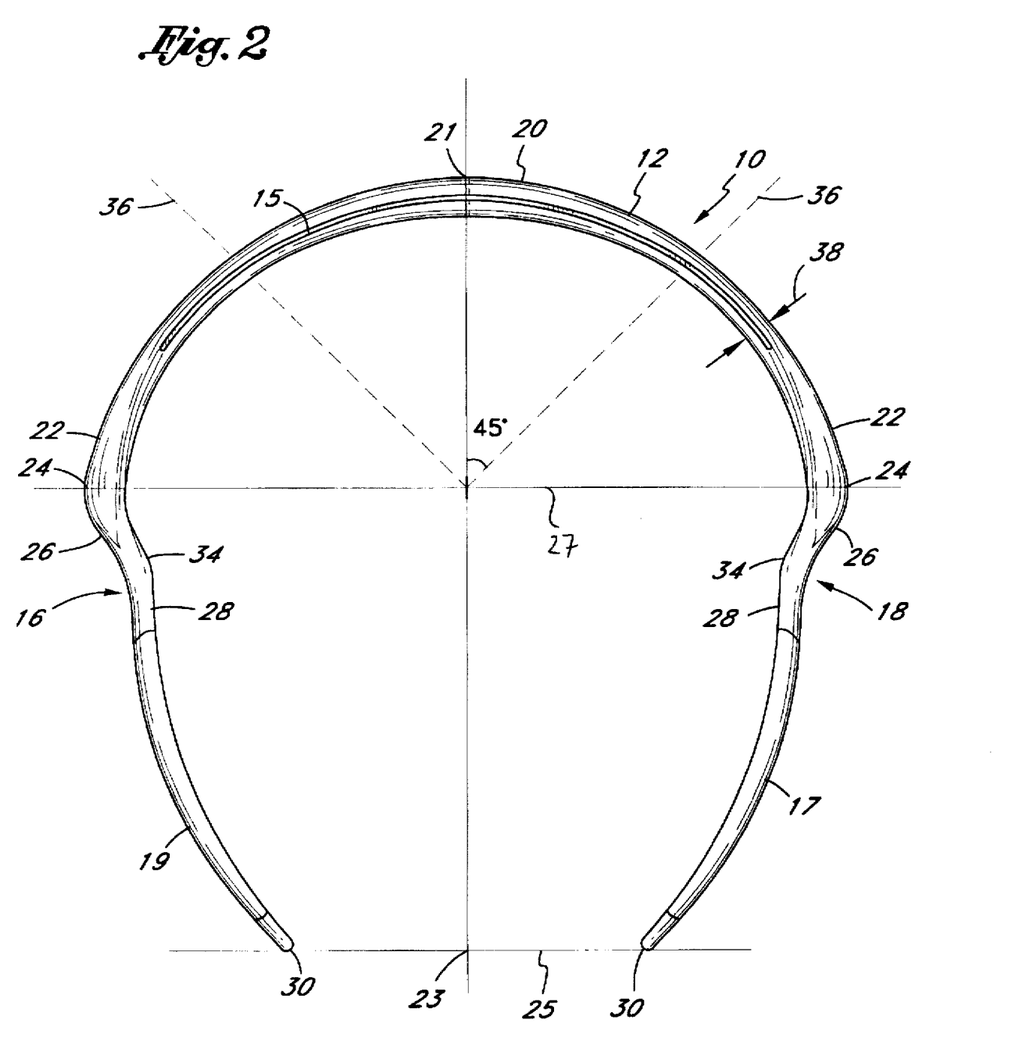
FIG. 2 is a bottom plan view of the eyeglass frame of FIG. 1.

Lens 14 may be secured to frame 12 either removably or permanently, such as by fitting at least a portion of the lens within a lens receiving slot 15, as shown in FIG. 2.

As shown in FIGS. 1 and 2, the frame 12 and earstems 16 and 18 are hingeless. In this embodiment, the frame 12 and earstems 16 and 18 comprise a single piece of material. The frame 12 may be conveniently molded or otherwise formed from various conventional eyewear frame plastics or a variety of other materials. The lens 14 may take any of a number of configurations and may be formed of thermoformed sheet plastic, injection molded plastic such as polycarbonate, or various other materials, as determined by the intended use of the lens. Preferably the lens is injection molded and mounted in the frame 12 in a manner that the lens substantially retains its as molded configuration. In its as molded condition, the lens may have, among others, a cylindrical or toroidal geometry. These geometries are disclosed in U.S. Pat. No. 4,859,048 to Jannard and 4,867,550 to Jannard the disclosures of which are incorporated herein by reference. Alternatively spherical lens geometry and other configurations can be readily utilized with the frame of the present invention.

In the preferred embodiment, the earstems 16, 18 may be provided with any of a variety of structures for improving retention of the eyeglass on the head of the wearer, such as elastomeric traction devices 17, 19. Such devices are disclosed and claimed in U.S. Pat. Nos. 5,054,903 and 5,137,342, the disclosures of which are incorporated herein by reference. Although the preferred embodiment of the present invention discloses use of the traction devices 17, 19, it can be appreciated that the invention can be practiced without the use of traction devices 17, 19.

As shown in FIG. 2, the earstems 16, 18 and the frame 12 include a right and left diverging section 22, a transition section 24, a converging section 26, and a retaining section 28. Due to the bilateral symmetry of the preferred embodiment, only one side will be described in detail. Preferably, the diverging section 22 extends laterally from the lens 14 and away from the opposing earstem to define an increasing lateral distance between opposing earstems 16 and 18. When used in cooperation with a curved unitary lens 14 and/or frame 12, the diverging section 22 may extend substantially along the arc of, or radially outward from, the frame 12.

Referring again to FIG. 2, the diverging section 22 terminates at the transition section 24. The transition section 24 represents the intersection of the diverging section 22 and the converging section 26. Preferably, the transition section 24 represents the greatest lateral distance between the opposing earstems 16 and 18, and as a consequence, the transition section 24 will normally be spaced apart from the head of the wearer. In the embodiment illustrated in FIG. 2, the transition section 24 is simply a bend in the direction of the earstem so that the earstem is angled back toward the head of the wearer in the posterior direction. Alternatively, the transition section 24 may have an elongated linear front to back length so that it extends up to the overall length of the earstem in the posterior direction.

The converging section 26 begins at the transition section 24 and inclines toward the opposing earstem 16 or 18, to define a decreasing lateral separation. The converging section 26 terminates at the retaining section 28, typically at a point 34 which is between ⅛ and ¾ the overall length of the earstem, and preferably is between about ⅛ and ½ the overall length of the earstem from the anterior end thereof. The retaining section 28 extends posteriorly to terminate at the distal end 30 of the earstem.

Preferably, the retaining section 28 is configured to employ an elastomeric traction device 17 or 19, as described in the above-referenced patents. The traction device 17 is in the illustrated embodiment disposed proximal to the distal end 30 of the earstem 18, and distal to the converging section 26 of the earstem 18. Preferably, the retaining section 28 includes an area of reduced cross sectional area such as an annular seat having a posterior shoulder (not shown) near distal end 30. The posterior shoulder is sized to provide a stop for elastomeric traction device 17 so as to prevent distal axial displacement of the traction device 17 under normal wearing conditions. The traction device 17 provides an outer surface which enhances the retention of the eyewear relative to the head by providing an increased coefficient of static friction between the eyewear and the head. A preferred material for the traction is KROTON G, manufactured by Shell Oil Company. The device 17 is preferably extruded or molded into a tubular configuration adapted to slide concentrically over at least a portion of the retaining section 28.

The retaining sections 28 of opposing ear stems 17, 19 converge in the distal (posterior) direction in the horizontal plane, as illustrated in FIG. 2. The combination of the frame 12 and the earstems 16, 18 cooperate to bias each earstem toward the opposing earstem when the earstems are separated in the as worn orientation.

In general, the upper frame 12 in accordance with FIGS. 1-3 of the present invention is smoothly sculpted to minimize the risk of stress fractures, while at the same time optimizing the strength and flexibility of the frame in the relevant dimensions as well as other advantages which will be described. For example, referring to FIGS. 2 and 3, a central region 20 of the upper frame 12 is provided with a minimal cross-sectional thickness in the front elevational view (vertical plane thickness). Structural integrity is maintained by lengthening the anterior to posterior thickness (horizontal plane thickness) in central region 20. See FIGS. 1-3.

Preferably, the vertical thickness of the upper frame 12 in central region 20 is in within the range of from about 0.100" to about 0.350", and preferably less than about 0.500". The anterior to posterior thickness in the region 20 is within the range of from about 0.220" to about 0.400" and preferably greater than about 0.100". In the illustrated embodiment, the vertical dimension through region 20 is about 0.246", and the anterior to posterior thickness in the central region 20 is about 0.350".

The vertical thickness of the frame decreases gradually to about 0.165" in the illustrated embodiment within about 45° around the frame from midpoint 21. The vertical thickness then increases to about 0.420" at about point 38 near the lateral end of the lens slot 15.

Travelling circumferentially around the arc of the upper frame 12 clockwise or counter clockwise from the midpoint 21 of central region 20, a relative minimum 38 is reached in terms of the thickness of the upper frame 12 in the radial direction. At that point, the vertical thickness through the frame has increased to as much as about 0.4" or more, and the thickness of the frame 12 in the radial (horizontal plane) direction has decreased to no more than about 90% or 80% or less of the radial thickness at midpoint 21. This encourages any horizontal plane flexing of the frame 12 to occur at the edge of or laterally of the lens connection slot 15 of the frame, thereby enabling the frame and earstems to accomplish the medial biasing function described herein throughout a range of earstem separations, while at the same time minimizing any flexing in the primary optical zone of the lens 14.

The minimum radial thickness point 38 is generally within the range of from about 35° to about 75° from midpoint 21. Preferably, point 38 is between about 40° and about 65° from midpoint 21.

At roughly 90° around the frame 12 from the midpoint 21, the thickness of the frame in the radial direction reaches a relative maximum, where it is within the range of from about 0.375" to about 0.410" thick. In the illustrated embodiment, the thickness in the radial direction of the frame at transition section 24 is about 0.395".

The present inventors have determined that by sculpting the upper frame in the foregoing manner, the structural integrity of the frame can be preserved while at the same time optimizing the optical zone of the lens by providing a minimal frame in the vertical direction. In addition, optical distortion through the lens as a result of flexing the lens when in use is minimized by the sculpting described above. Furthermore, the eyeglass is relatively streamlined from an aerodynamic standpoint, so that a minimal vertical cross-section is encountered by oncoming wind, and weight can be minimized by eliminating structurally unnecessary material.

Figure 3:
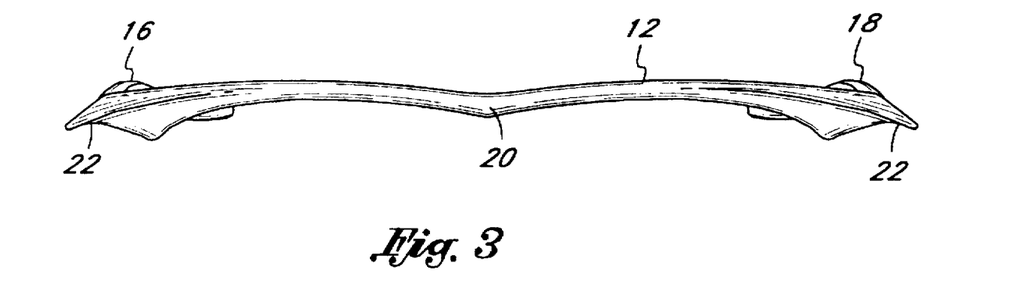
FIG. 3 is a front elevational view of the eyeglass frame of FIG. 1.

The eyeglass frame 12 is further provided with a lateral ridge 22, extending laterally from the upper frame 12 as seen in FIG. 3. Lateral ridge 22 increases the relative strength of the eyeglass frame 12 in the horizontal plane, and may provide aerodynamic advantage by minimizing the vertical cross-sectional area of the frame. In addition, the lateral ridge 22 ramps relatively downwardly in the posterior direction when the wearer is oriented in the normal straight ahead orientation. This ramped lateral ridge 22 may accelerate oncoming air past the notch 32 formed between the lens 14 and the frame 12, to increase venturi-driven ventilation behind the lens. This may be beneficial in certain lens designs to reduce the occurrence of fogging which may result by air entrapped between the lens and the wearer's face.

Retention of the eyewear 10 is also improved by elongated earstems 17 and 19, which extend relatively far in the posterior direction. For example, the linear anterior to posterior dimension from the front of the frame at midpoint 21 to point 23 which corresponds with the distal tip 30 of earstems 17 and 19 (see FIG. 2) is generally greater than about 6.0" and preferably within the range of from about 6.5" to about 7.5". In the illustrated embodiment, the dimension is about 6.83". The overall outside circumference of the eyewear from tip 30 on earstem 16 around the frame 12 to tip 30 on earstem 17 is normally greater than about 18" and preferably within the range of from about 18.25" to about 19.25" for adult eyewear. In the illustrated embodiment it is about 18.625".

When the eyeglasses are in an unstressed orientation, as illustrated, the linear separation along an axis 25 between distal points 30 on earstems 17 and 19 is generally within the range of from about 1.75" to about 3.00". Preferably, the separation between tips 30 in the unstressed configuration will be within the range of from about 2" to about 4" without the lens mounted in the frame.

The neck circumference for the normal adult wearer is generally within the range of from about 14" (usually female) to about 15" (usually male). Neck sizes as high as about 17.5" or higher may be found in some individuals, and neck sizes as low as about 13" may be found in the adult population. The preferred unstressed separation along axis 25 between the posterior ends of the opposing earstems is thus sufficient to allow the eyewear to be hung around the neck of the typical adult wearer. In addition, referring to FIG. 2, the separation between opposing earstems increases from a minimum at about distal tips 30 to a maximum at about axis 27. The interior separation between earstems at about axis 27 is generally in the range of from about 5.2" to about 5.75" or greater. In this manner, the eyewear can be comfortably advanced around the neck of the wearer and be retained there without applying any material compressive pressure to the wearer's neck.

In the illustrated embodiment, the linear separation along axis 25 between distal tip 30 on earstem 16 and distal tip 30 on earstem 17 is no more than about 3 inches in the unstressed orientation. In the as worn orientation, the distal tips 30 will be separated significantly to accommodate the head of the wearer. Although head size will vary considerably from individual to individual, the as worn separation along an axis 25 between tip 30 on earstem 16 and tip 30 on earstem 18 will normally be within the range of from about 4.0" to about 5.5" or larger for adult wearers. Thus, the design and construction materials of the eyeglass 10 must normally accommodate a range of motion such that the distance along axis 25 separating the opposing earstems can increase by as much as about 100% and preferably 200% or more without cracking or exceeding the elastic limit of the eyeglass frame 12 and earstems 16 and 18. Preferably, as has been discussed, substantially all of the motion will be absorbed by the earstems and portions of the frame 12 disposed laterally and to the posterior of the primary optical zone of the lens 14.

Each earstem 16 and 18 is preferably inclined in the medial direction over a length from about point 34 to the distal tip 30. The incline may further be provided with a curvature which is concave in the medial direction as illustrated. Although the curvature can be constant radius or nonconstant radius, it roughly approximates a curve having a radius within the range of from about 4.5" to about 3.5". When the distal ends 30 of earstems 16 and 18 are separated in the lateral direction for the purpose of wearing the eyeglasses, at least some of the stress is absorbed by flexing in the region from about 34 to 30, as well as at or about point 38 on the frame. This flexing can enable the eyeglass frame 12 to provide a medially directed bias at distal ends 30 throughout a wide range of head widths, while at the same time minimizing any induced optical distortion on the lens 14 due to flexing of the upper frame 12 in and around central region 20.

The posteriorly elongated earstems of the present invention, combined with the medially inclined nonstressed orientation cooperate to provide a medially directed bias against the head of the wearer. Due to the posterior elongation of the earstems, the distal regions of the earstems contact portions of the wearer's head which are inclined medially in the posterior direction. This is a result of the combination of the length and bias of the earstems with the head shape of the normal wearer which is generally oval or otherwise rounded on the posterior side. The medial bias on the earstems causes the earstems to try to seat as far back on the wearer's head as possible. This combination produces a pulling force on the eyeglasses 10 which tends to retain the eyeglass on the head of the wearer. This posterior bias on the eyeglasses can be accomplished without the need for a conventional strap to extend around the rear of the wearer's head, as is conventional with action sports goggles.

Figure 4:
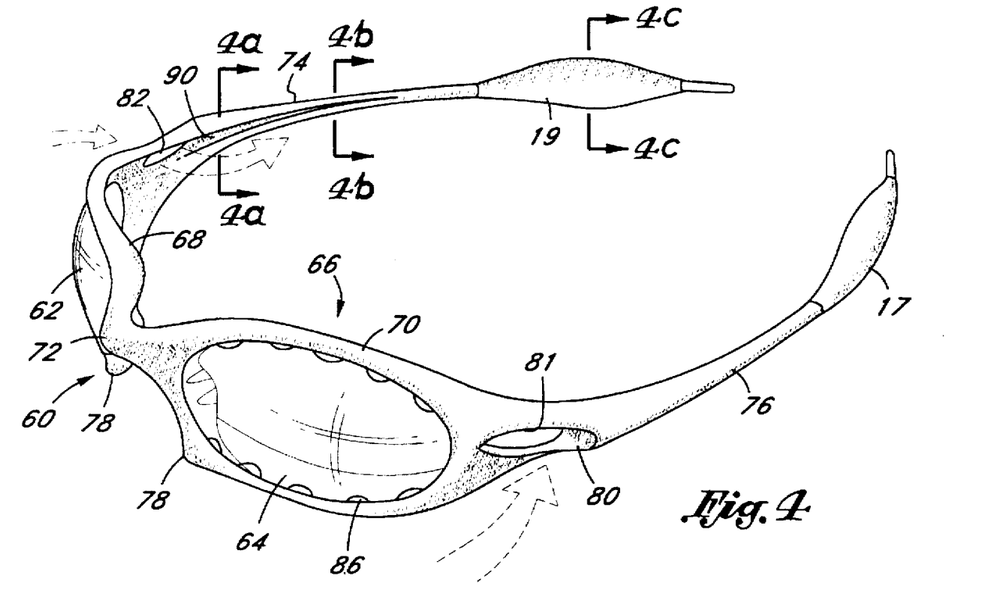
FIG. 4 is a front perspective view of a dual lens pair of eyewear embodying the unitary frame of the present invention.

Referring to FIG. 4, there is disclosed a dual-lens hingeless eyeglass system 60. The eyeglass system 60 generally comprises a right lens 62 and a left lens 64 mounted in an eyeglass frame 66 and adapted to be positioned in the wearer's line of sight. Eyeglass frame 66 comprises a right annular orbital 68 for supporting right lens 62 and a left annular orbital 70 for supporting left lens 64. The right orbital 68 and left orbital 70 are connected by way of a bridge 72.

A right earstem 74 and a left earstem 76 are molded in a hingeless singular piece construction with the eyeglass frame 66. The earstems 74 and 76 may be provided with any of a variety of structures for improving retention of the eyeglass on the wearer's head, such as conventional hook shaped rearward portions, or elastomeric traction devices 17, 19 as have been discussed.

Similar to the previously disclosed embodiments of the invention, the earstems 74 and 76 are elongated in the posterior direction to wrap around at least a portion of the rear of the wearer's head for improved retention. The elastomeric traction devices 17 and 19 in the present embodiment have an axial length within the range of from about 1.5" to about 2.5" and a vertical height within the range of from about 0.4" to about 0.7". Preferably, the axial length of the elastomeric traction device 17 or 19 is less than about 60% of the overall length of the earstem from the lateral edge of the closest lens.

Figure 4A:
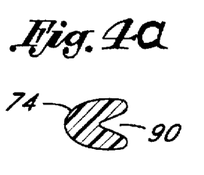
FIGS. 4a though 4c illustrate cross-sectional elevational views through the earstem on FIG. 4.
Figure 4B:
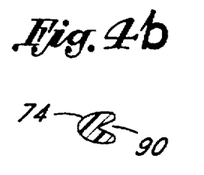
Figure 4C:
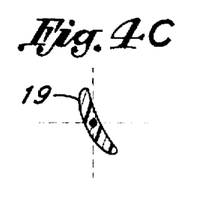

The elastomeric traction device 17, 19 is preferably slightly concave towards the wearer in both the horizontal and vertical planes. In addition, the elastomeric traction device 17, 19 is canted slightly within the range of from about 3° to about 15° from vertical, to better conform to the typical confirmation of the wearer's head. See FIG. 4c. Canting of the elastomeric traction devices 17, 19 is accomplished in a direction such that the medially facing surface of the elastomeric traction device 17, 19 faces slightly upward in the medial direction.

Preferably, the eyeglass frame 66 including orbitals 68 and 70 and bridge 72 are relatively rigid so that the orientation of the right lens 62 with respect to the left lens 64 remains substantially unchanged throughout the anticipated range of motion of earstems 74 and 76. In other words, as earstems 74 and 76 are separated laterally to accommodate the head of a wearer, flexing occurs primarily along the length of the earstem 74 and 76, and, to a lesser extent, in the area of side air inlets 80, 82 as will be discussed. For this purpose, the earstem 74 and 76 taper to a relatively minor cross sectional dimension from about their midpoint to their distal ends, compared to the cross sectional dimension of the structural component of the eyeglass frame surrounding the lenses and in the bridge region. Maintaining the orientation of the right and left lens substantially unchanged with respect to each other whether or not the eyeglasses are being worn, and throughout a wide range of head sizes in the as worn orientation minimizes the introduction of prismatic distortion as will be appreciated by persons of skill in the art.

In one ventilated frame aspect of the present invention, a side air inlet 80, 82 is included on the lateral side of the lens retaining section of the frame such as each of orbitals 68 and 70. The inlets 80, 82 constitute an independent inventive feature, such that they may advantageously be used in hingeless or conventionally hinged eyewear frames, and in either dual lens or unitary lens system. The vented frame disclosed herein may also be used with or without additional ventilation features, such as the vented lens illustrated in FIGS. 4 and 5.

In the preferred embodiment, each of the side air inlets 80, 82 lies on a plane which resides at a forward-facing angle with respect to the eyeglasses. This allows the air inlet to face forward into the air stream when worn (see FIG. 5), and capture air at a flow rate which is commensurate to the relative wind speed at the face of the wearer. Orientation of the side air inlets 80, 82 is thus preferably accomplished with reference to the orientation of the eyeglasses in the as-worn orientation.

For example, eyeglasses may be conceptualized to be bilaterally symmetrical about a medial longitudinal axis which extends in parallel to the wearer's normal line of sight through the lenses. The normal line of sight may be defined as the straightahead line of sight in which there is neither deviation in the vertical nor horizontal plane. Traditional dual-lens eyeglasses often contained lenses which lie on a plane extending at a perpendicular to the normal line of sight.

An air inlet 80 or 82 which lies on a plane perpendicular to the normal line of sight would thus possibly optimize air flow, but be unacceptable from a design standpoint in many eyeglass designs. The side air inlet 80, 82 may also be oriented on a plane which is parallel to the normal line of sight. However, that vent would experience primarily only passive air flow in response to forward movement of the wearer. Preferably, therefore, the side air inlets 80, 82 each lie on a plane which resides somewhere between parallel to and perpendicular to the normal line of sight. Preferably, each plane containing each air inlet 80 and 82 resides at an angle within the range of from about 5° or 10° to about 70° or 80° with respect to the normal line of sight. In a preferred embodiment, the side air inlets 80, 82 each lie on a plane which resides within the range of from about 35° to about 55° from the normal line of sight. Air may also be directed through frame vents by providing air deflection surfaces such as wind scoops which will deflect oncoming wind through the vents.

Figure 5:
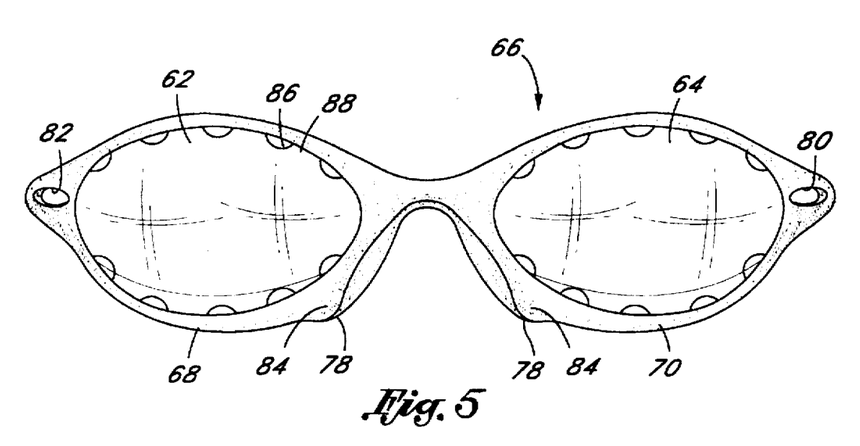
FIG. 5 is a front elevational view of the eyewear in FIG. 4.

The amount of air drawn through each side air inlets 80, 82 is a function of the apparent cross sectional area of the aperture, when viewed from the front along a parallel to the normal line of sight. See, for example, elliptically shaped vent 80 in FIG. 4, which appears closer to circular in shape when viewed head-on as shown in FIG. 5. An apparent forward facing vent can be accomplished through a wide variety of shaped apertures, depending upon the thickness of the earstem and frame, and the contouring. In general, the plane referred to above on which the vent resides is the plane of the outer edge 81 of the vent 80 as seen in FIG. 4. However, in highly contoured embodiments, the plane referred to above could deviate from the outer edge 81 of the aperture 80 as will be apparent to those of skill in the art in view of the disclose herein. In addition, the use of air deflecting wind scoops renders the precise orientation of the vent less important as will be appreciated by those of skill in the art.

The side air inlets 80, 82 in a preferred embodiment of the invention cooperate with optional corresponding channels 90 in each of the earstems 74 and 76. Channel 90 extends in a posterior direction along the medial side of each earstem, and gradually reduces in channel volume in a rearward direction. See, for example, FIG. 4a and 4b. The provision of a channel 90 or other contouring on the medial side of the earstem can increase the apparent forward facing cross sectional area of the air inlets 80 and 82, while keeping a low lateral profile, thereby potentially optimizing air flow through the air inlets 80, 82. Optimizing air flow through side inlets 80, 82 can improve the venturi driven ventilation across the inside surface of the lenses, to minimize the occurrence of fogging.

The cross sectional configuration of the vent 80 can be varied as will be appreciated while still achieving the functional objective disclosed herein. Elliptical vents as illustrated, circular vents or other shapes may be used.

The cross sectional area of the vent can also be varied depending upon a variety of factors, such as the extent to which the vent is forward facing, and the size and angle of any wind deflection surfaces. In general, the cross sectional area of the vent will be equivalent to the area of a circle having a diameter of at least about ⅛ inch and preferably at least about 3/16 inch or ¼ inch. Areas as large as the area of a circle having a diameter of ⅜ inch or ½ inch or larger can also be used, depending upon the overall dimensions of the earstem and eyeglass orbitals.

When the eyeglass system 60 is worn, air is drawn into the side air inlets 80, 82 during forward motion. The force of the air as it is directed around the head of the wearer may create a venturi effect about the lenses 62 and 64. The venturi effect created by the side air inlets 80, 82 aids in drawing air through the apertures 86 as will be discussed and/or over the top and under the eyeglasses, thereby improving ventilation and fog resistance.

Fairings or projections 78 may also be provided on the medial side of each orbital 68 and 70. The fairings 78 function to deflect the air contacting the eyeglass system 60. For this purpose, each fairing 78 is provided with a wind deflecting surface 84 which is inclined laterally in the posterior direction to provide a ramp that deflects oncoming wind laterally across the lens 62, 64. The surface 84 can be contoured to deflect wind through one or more adjacent apertures 86 as will be discussed. By redirecting some portion of air flow, the fairings can increase the amount of available air flowing through both the apertures 86 and the side air inlet 80. Preferably, fairings 78 are integrally molded with the corresponding orbitals 68, 70.

Referring to FIG. 5, lens 62 is provided with a plurality of apertures 86, separated from each other by lens portions 88 for connecting the lens 62 to the orbital 68. In most embodiments of the present invention, the right and left lenses will be mirror images of each other. Accordingly, the apertures 86 will for simplicity be discussed only in connection with a single lens 62.

One of the advantages of the design of the present invention is the ability to provide ventilation apertures 86 in a relatively small lens, while at the same time minimizing interference with the optical zone of the lens. In the embodiment illustrated in FIGS. 4 and 5, this is accomplished by positioning the aperture 86 such that at least a first portion of the circumference of the aperture is formed by the lens and at least a second portion of the circumference of the aperture is formed by a portion of the frame. In an alternate embodiment of the invention, the entire circumference of the aperture may be surrounded by the frame.

Apertures can alternatively be positioned in the lens spaced apart from the frame, if the overall lens area is large enough to produce a sufficient uninterrupted optical zone for the desired application. Apertures may alternatively be formed by a plurality of enclosed circles punched into the peripheral zone of the lens, which circular holes are partially covered by the frame to produce the appearance of a plurality of semicircles.

As will be apparent to those of skill in the art, the cross-sectional shape of the aperture can take any of a variety of forms and still accomplish the objectives of the present invention.

The circular or semi-circular indent in the lens which forms aperture 86 in the illustrated embodiment can have a constant or substantially constant radius. Alternatively, the aperture 86 can take any of a variety of alternate forms as will be apparent to those of skill in the art in view of the disclosure herein. For example, the aperture may be defined by a portion of or all of a circular, semicircular, oval, elliptical, or non regular curved shape depending upon the shape of the recess or aperture and upon its orientation once mounted in the frame. Angular configurations such as triangular, square, rectangular, slotted, or others having sharp corners can be used but tend to be less desirable if they have sharp corners due to stress dispersion considerations as will be apparent to those of skill in the art. However, the provision of radiused corners in an otherwise angular geometry can minimize the risk of lens fracture. Thus, for example, elongated rectangular apertures with slightly rounded corners can be provided to extend along the interface between the frame and the lens.

The cross-sectional size or area of the aperture 86 can also be varied considerably and remain within the scope of the present invention. Relevant size considerations include the cross-sectional area of each individual aperture 86, the sum of all of the cross-sectional areas of all apertures 86 on a given lens, the location and distribution of the apertures on the lens, and the size of the desired aperture free optical zone. To achieve a desired total cross-sectional flow area, fewer relatively larger apertures 86 may accomplish the same flow objective as relatively more smaller cross-sectional area apertures 86. In general, the size and number of apertures 86 to achieve a desired total flow area can be optimized depending upon a variety of competing considerations such as desired impact strength for the lens, desired flow distribution across the lens, and the acceptable distance into the optical zone that the apertures 86 can project.

In general, the total cross-sectional flow area of the apertures 86 in the lens will generally range from about 0.2% to about 50% of the total lens area. Preferably the flow area of the apertures will be in the range of from about 0.5% to about 20% of the total lens area, and, more preferably, between about 1% and about 10% of the total lens area.

The minimum number of apertures is affected by a variety of factors, including desired air flow and other aspects of the eyeglass design. For example, if the eyewear conforms very closely to the wearer's head, at least one lower edge aperture and at least one upper edge aperture is preferred to permit a convection flow. Preferably, four or more apertures are provided at each of the upper and lower edges. In terms of area, each of the lower and upper edges is preferably provided with apertures totalling at least about 0.2% and more preferably at least about 1% of the total area of the lens. Apertures can be positioned along the top or the bottom edges or either side, or any combination thereof.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the appended claims.

What is claimed:

1. A hingeless eyeglass frame for receiving a separate lens, comprising:

an arcuate lens support section for extending across the front of the face of a wearer to support at least one lens in the wearer's line of sight, said support section having a central zone and first and second lateral zones, said support section further having a recess in the frame for receiving at least one lens; and first and second earstems extending from the first and second lateral zones such that when the frame is on the front of the wearer's head the first and second earstems extend posteriorly from the lens support section, past the wearer's ears, and towards each other partway around the back of the wearer's head, said first and second earstems terminating in first and second posterior ends;

each of said earstems concave in a medial direction and having a separation between the first and second posterior ends within the range of about 2 inches to about 4 inches in an unstressed orientation;

wherein the eyeglass frame is of a hingeless unitary construction.

2. A hingeless eyeglass frame as in claim 1, wherein the first and second earstems are separated laterally from each other by at least about 5.2 inches in the relaxed, unworn configuration, at at least one point between the posterior ends and the lens support section.

3. A hingeless eyeglass frame as in claim 2, wherein the first and second ends are moveable in a lateral direction throughout a lateral range of motion to a separation distance of at least about 4.00", while maintaining a medially directed bias throughout said lateral range of motion.

4. A hingeless eyeglass frame as in claim 3, wherein the curvature of the eyeglass frame throughout said arcuate lens support section remains substantially unchanged while said first and second ends are advanced throughout said lateral range of motion.

5. The frame of claim 2, in which the distance between the ends of the earstems can be increased by up to 100% beyond the distance corresponding to the relaxed unworn 6. The frame of claim 2, in which the linear dimension from the front of the frame at its center to the midpoint between the posterior ends of the earstems is within the range from about 6 to about 7.5 inches.

7. A hingeless eyeglass frame as in claim 1, comprising an integrally molded polymeric material.

8. A hingeless eyeglass frame as in claim 1, further comprising first and second lens orbitals on said arcuate lens support section.

9. The frame of claim 1, in which the frame includes, on both sides of the central zone first and second relative minimums in the radial thickness of the frame, said minimums having a smaller dimension than at least one radial thickness in each of the first and second lateral zones.

10. The frame of claim 9, in which the relative minimums are located near respective ends of the recess.

11. The frame of claim 9, in which the radial thickness minimums are located within the range of from about 35 degrees to about 75 degrees away from the wearer's straight ahead line of sight.

12. The frame of claim 11, in which the radial thickness minimums are located between about 40 degrees and about 65 degrees away from the wearer's straight ahead line of sight.

13. The frame of claim 1, in which the vertical thickness of the frame in the central zone is within the range from about 0.1 to about 0.5 inches;

the anterior to posterior thickness of the frame in the central zone is within the range from about 0.1 to about 0.4 inches; and the vertical thickness of the frame is greater than about 0.4 inches at relative minimums in the radial thickness of the frame, the radial thickness of the frame at the relative minimums being less than about 90% of the radial thickness of the frame at the midpoint of the central zone.

14. The frame of claim 13. wherein the thickness of the frame in the vertical direction at about 90 degrees away from the wearer's line of sight along the arc of the frame is in the range from about 0.375 to 0.41 inches.

15. The frame of claim 1. further comprising a lateral ridge extending laterally from the top of the frame for increasing the relative strength of the frame in the horizontal plane.

16. The frame of claim 1. in which the maximum interior separation between the earstems is in the range of from about 5.2 to about 5.75 inches. so that frame can be comfortably advanced around the neck of the wearer and retained there without applying any material compressive pressure to the wearer's neck.

* * * * *

UNITED STATES PATENT AND TRADEMARK OFFICE
CERTIFICATE OF CORRECTION

PATENT NO. : 5,760,868
DATED : June 2, 1998
INVENTOR(S) : James H. Jannard and Peter Yee It is certified that error appears in the above-indentified patent and that said Letters Patent is hereby corrected as shown below:

In Claim 5, column 12, line 31, after unworn, please add

--configuration, while substantially all of the motion is absorbed by the earstems and portions of the frame disposed laterally and to the posterior of the central zone.--

Signed and Sealed this

Twelfth Day of October, 1999

Attest:

Q. TODD DICKINSON

*Attesting Officer*   Acting Commissioner of Patents and Trademarks